United States Patent [19]
Thom

[11] 4,105,667
[45] Aug. 8, 1978

[54] IMIDAZOLE TYPE CURING AGENTS

[75] Inventor: Karl Friedrich Thom, St. Paul, Minn.

[73] Assignee: Minnesota Mining and Manufacturing Company, St. Paul, Minn.

[21] Appl. No.: 55,981

[22] Filed: Jul. 17, 1970

[51] Int. Cl.$^2$ .................. C07F 15/00; C07F 3/00; C07F 1/00

[52] U.S. Cl. .................. 260/299; 260/18 EP; 260/824 EP; 260/832; 528/90; 528/361

[58] Field of Search ..................... 260/299

[56] References Cited
U.S. PATENT DOCUMENTS 3,310,570 3/1967 Middleton .................. 260/299
3,502,689 3/1970 Biletch .................. 260/299

Primary Examiner—Donald G. Daus
Assistant Examiner—Diana G. Rivers
Attorney, Agent, or Firm—Cruzan Alexander; Donald M. Sell; Warren R. Bovee

[57] ABSTRACT

The disclosed curing agents or initiators have the formula $ML_n(O-SO_2-R_f)_m$ wherein L is an imidazole, M is a metal, $n$ is a coordination number of M, $R_f$ is a fluorinated alkyl group, and $m$ is the valence of M. These curing agents are useful in latent curable epoxy systems. Upon heating to the cure temperature (e.g. 100° – 250° C.), such systems cure efficiently and with a low exotherm.

5 Claims, No Drawings

IMIDAZOLE TYPE CURING AGENTS

This invention relates to coordination compounds which are useful as latent initiators (i.e. curing, hardening or activating agents). An aspect of this invention relates to low-exotherm curing of strained heterocyclic systems such as epoxides (oxirane ring-containing compounds) or the like. A further aspect of this invention relates to a one-part system comprising a curable epoxide and a fluoroalkylsulfonate salt of a metal coordinated with imidazole or substituted imidazole ligands.

It is well-known that the oxirane or 1,2-epoxy group, similar strained heterocyclic groups, and similar polymerizable or crosslinkable systems are subject to attack by a proton or by the unbonded electron pair of an amino nitrogen. Both imidazole and its substituted derivatives (hereinafter collectively referred to as "imidazoles" or as "the imidazole nucleus") have been investigated as initiators, e.g as curing agents for epoxy resins, and have been found to produce cured (i.e. polymerized and/or crosslinked) resins with good properties; see for example, Paul F. Bruins, Ed., *Epoxy Resin Technology*, Interscience Publishers, N.Y. (1968) and Farkas et al, *J. Applied Polym. Sci.*, 12, 159 (1968). Unless the 1-position of the imidazole nucleus is either blocked in some manner (e.g. see U.S. Pat. No. 3,356,645 to Warren, issued Dec. 5, 1967) or quaternized, it contains a secondary (1-unsubstituted) or tertiary (1-mono-substituted) nitrogen with an unbonded electron pair. This electron pair is ordinarily quite reactive with the 1,2-epoxy group even at relatively low ambient temperatures; therefore, imidazoles are not considered "latent" curing agents or initiators. In this art, a "latent" curing agent or initiator is one which does not react readily with the oxirane ring (or similar strained heterocycles) at ordinary ambient temperatures, but which can be made to react readily under certain specific conditions, e.g. elevated temperatures. Typically, such elevated temperatures are above 50° C. and, in industrial practice, above 100° C. A latent curing agent or initiator can therefor be included in a one-part curable system which is storable (i.e. will remain substantially free of gelling or hardening due to polymerization or crosslinking) for long periods of time. Stated another way, the pot life of a curable resin/"latent" curing agent mixture is extremely long unless the mixture is heated.

German Offenlegungsschrift (DOS) No. 1,904,641 (laid-open date, Nov. 6, 1969) discloses a class of curing agents obtained by reacting imidazoles with certain metal salts; the resulting products are referred to as "metal salt complex compounds of imidazoles". Theoretical studies report that the imidazole nucleus can be a ligand for metals of Groups VIII, IB, II (A and B), and VII B. Such studies are evidence for the proposition that the cationic portion of the metal-imidazole salt "complex compounds" described in DOS 1,904,641 consists of a metallic cation combined with an appropriate (coordination) number of imidazole ligands. See, for example, J. Am. Chem. Soc. 76, 3054 and 6219 (1954), 77, 859 and 5291 (1955), 78, 260 (1956), and 80, 5033 (1958); J. Chem. Soc. 1961, 4790, (A) 1967, 757 and (A) 1969 368. This proposition is not entirely supported by the disclosure of DOS 1,904,641 in view of the teaching on page 5 that the metal salt/imidazole molar ratio is "not critical" and can be between 1:1 and 1:6; the literature establishes that the number of moles of imidazole is a small integer greater than 1, this integer being fixed by the various possible coordination number or numbers of the metal, e.g. 2, 3, 4, or 6. The making of a metal salt/imidazole coordination compound which consists of an equivalent of metal and a single mole or fractional number of moles of imidazole has never been reported and would be contrary to established principles of coordination chemistry. Apparently the aforementioned DOS teaching merely describes the amount of imidazole starting material to be used and does not represent an analysis of the "complex".

The initiation reaction, which activates a system containing a strained heterocycle and leads to gelling or curing (hardening) due to polymerization, crosslinking, etc. is wellknown. For imidazole-type initiators (including prior art types and the initiators of this invention), the 1-nitrogen of the imidazole nucleus or moiety reacts with the strained heterocyclic ring according to the following equation:

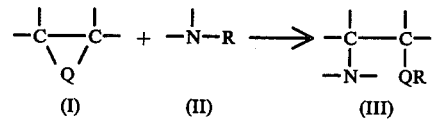

In this equation compound (I) contains at least one strained heterocyclic ring, Q being, for example, oxygen or N-Y, wherein Y is an organic radical. Compound II is an imidazole, only the 1-position being shown, and the R substituent is hydrogen or an organic radical such as a lower alkyl group. Compound (III) is the product of the initiation reaction, i.e. the material obtained by cleavage of the heterocyclic ring. See Lee et al, *Handbook of Epoxy Resins*, N.Y., McGraw-Hill, 1967, Chapter 5, pp. 5-1 and 5-2. Further reactions can, of course, occur after compound (III) is formed, e.g. polymerization of compound (I) or crosslinking of polymer chains if compound (I) is already a polymer or prepolymer.

The reaction represented by the above equation is strongly exothermic. The exotherm of a curable epoxy compound is defined as "the increase in temperature of the compound above the cure temperature due to energies released as the epoxy groups react." Lee et al, op. cit., Chapter 17, page 17-8. The higher the exotherm, the more likely that detrimental effects will be observed during curing, e.g. gas formation, explosions, uneven gelling, shrinkage, and charming or similar thermal degradation. Lee et al, op. cit., pp. 17-9 and 17-10. These detrimental effects are most commonly encountered with massive or relatively thick, as opposed to "film- or layer-like" castings, i.e. castings with geometrically solid shapes having a significant third dimension or a high volume-to-area ratio. Rapid curing of a typical epoxy resin casting using the latent curing agents of DOS 1,904,641 or similar latent curing agents requires heating the casting to a temperature referred to by Lee et al as the "cure temperature". This temperature is not necessarily the only temperature at which hardening due to crosslinking or polymerization or the like will be initiated. Rather, it is the temperature, or range of temperatures, at which complete curing to a hard material is efficient and rapid and produces a cured (polymerized and/or crosslinked) material with good properties. Typically, an epoxy resin casting is heated quite slowly to the "cure temperature", which is ordinarily somewhere in the range of 100° - 200° C. and generally at least 120° C., in order to avoid the detrimental effects of a high exotherm. For a three dimensional casting (e.g. a 20 mm [diameter] × 30 mm [length] cylinder) comprising 10 g. of a typical one-part epoxy material such as the polyglycidyl ether of bisphenol A and epichlorohydrin and an appropriate amount of a preferred prior art metal-imidazole "complex" such as nickel or copper chloride-imidazole, the center of even this small casting would reach a peak exotherm temperature at least 130° C. above the "cure temperature", if the casting were heated to the "cure temperature" in a few minutes or less, e.g. by immersion in a preheated bath. Such peak temperatures are, in many instances, high enough to cause at least some of the detrimental effects described by Lee et al. Thus, the use of such prior art curing agents involves slowly heating the massive casting to the cure temperature. This slow heating is economically wasteful and not always effective in mitigating degradation cause by high exotherms. A further problem encountered in the application of these prior art curing agents is that many of these agents will not cure cycloaliphatic epoxides.

Accordingly, this invention contemplates initiators or curing agents of the metal salt-imidazole type wherein the exotherm caused by the opening of a strained heterocyclic ring is adequately controlled, i.e. is kept within non-degradative limits.

This invention also contemplates a curable epoxy system containing a latent curing agent or initiator, the system having a curing temperature which is preferably above 100° C., wherein the peak exotherm temperature reached during curing is significantly below the temperature at which undesirable side effects (e.g. charring) occur, regardless of how quickly the curable epoxy system is brought to the cure temperature.

Briefly, this invention involves the use of a particular class of metal salts which react with imidazole nuclei to form latent initiators or curing agents which efficiently and controllably initiate ring-opening reactions, e.g. the curing of epoxy compounds (including cycloaliphatic epoxides) at temperatures above 50° C. without causing unduly high peak exotherm temperatures.

The salts of this class (which are known per se or can readily be obtained from the corresponding fluoroalkylsulfonic acids, see U.S. Pat. No. 2,732,398 to Brice et al, issued Jan. 24, 1956) can be represented by the formula:

In formula (IV), M is a metal of groups VIII, IB, II(A and B), IIIA, IV(A and B), VIB, or VIIB of the Periodic Table. The transition metals (metals of the "B" Groups and Group VIII) are preferred, particularly Group VIII and Groups IB and IIB, which are especially suitable in the context of this invention. The metals of the first triad of Group VIII (Fe, Ni, Co) and copper, cadmium, and zinc are quite desirable from an economic standpoint. Silver is economical as compared to either gold or the noble metals of Group VIII.

The term $R_f$ designates a $C_1 - C_{18}$ fluorinated alkyl group wherein the carbon atom alpha to the sulfonyl radical has its other three valence bonds taken up by fluorine atoms or fluorinated alkyl substituents. $R_f$ is preferably a perfluorinated straight or branched-chain or cyclic alkyl group of 1-18 (preferably 1-8) carbon atoms, e.g. $CF_3$, $C_2F_5$, $n-C_3F_7$, $i-C_3F_7$, $n-C_8F_{17}$, perfluorocyclohexyl, perfluoro (4-methylcyclohexyl), 2-perfluorocyclohexyl perfluoroethyl, etc.

Suitable less highly fluorinated $R_f$ radicals include $HCF_2CF_2$, $C_3F_7CHFCF_2$, $(CF_3)_2CHCF_2$, $CF_3$-CFCl-$CF_2$, $ClCF_2CF_2$, and the like. In no case should a hydrogen substituent be located on the carbon alpha to the sulfonyl.

The term $m$ is a number from 1–4, preferably from 1 to 3. Thus, the preferred salts contain iron (II), iron (III), Co(II), Co(III), Ni(II), copper (I), copper (II), cadmium, zinc or silver cations and the corresponding stoichiometric number of perfluoroalkylsulfonate anions.

The salts of formula (IV) are reacted with a suitable imidazole (i.e. imidazole or a substituted imidazole) to provide the latent curing agents of this invention, which agents can be represented by the following formula:

wherein L is the ligand (the imidazole or substituted imidazole ) $n$ is a whole number ranging from 2–12 (preferably 2–8), and $R_f$ and $m$ are as defined previously.

Suitable imidazoles include imidazole itself (NH—CH=N—CH=CH) or a derivative thereof substituted at the 1, 2, 4, and/or 5 positions (the 1-position is the secondary or "pyrrole" nitrogen, =NH, and the 3-position is the "pyridine" nitrogen, =N-), but the 1-substituted imidazoles tend to be very slow to react, even at the cure temperature, and are not preferred except for applications where very slow cures are desirable. Thus, it is preferred that L have the following formula:

wherein $R_1$, $R_2$, and $R_3$ are the same or different and can be hydrogen, halogen, or an organic radical such as a hydrocarbon or substituted hydrocarbon radical, e.g. alkyl (preferably lower alkyl including aryl-substituted alkyl), aryl (preferably monocyclic aryl such as phenyl), aralkyl, alkenyl (e.g. vinyl, allyl), and other substituents known in the art (see, for example, the aforementioned U.S. Pat. No. 3,356,645 and DOS 1,904,641) and $R_1$ and $R_2$ can together comprise the atoms of a fused ring such as the three or four atoms of a cyclopentene or cyclohexene ring, a benzene ring or the like, and $R_1$ or $R_2$ together with $R_3$ can comprise the atoms of a fused N-heterocyclic ring. For efficient curing at the curing temperature, it is preferred that $R_4$ be hydrogen. If the $R_4$ substituent is not hydrogen, it can be similar to $R_1$, $R_2$, or $R_3$. Examples of preferred compounds of Formula (VI) are imidazole; 2-methyl imidazole; 2-ethyl imidazole; 2-ethyl, 4-methyl imidazole; 2,4-dimethyl imidazole, 2,4-diethyl imidazole; 2,4,5-trimethyl imidazole; 2-benzyl imidazole; 2-benzyl, 4-methyl imidazole; and 2-phenyl imidazole. The 1-substituted imidazoles are, as has been pointed out, also operative, and examples of these are 1-methyl imidazole, 1,2-dimethyl imidazole, and 1-phenyl, 2-methyl imidazole.

The compounds of Formula (V), which are not reported in the literature, are obtained by mixing a salt of Formula (IV) with an excess over stoichiometry of an imidazole of formula (VI) and subjecting the mixture to mild heat. The resulting product can be purified by extracting the excess imidazole or imidazole derivative using conventional extraction techniques and a suitable solvent such as toluene. The "stoichiometric" amount of the imidazole of Formula (VI) is determined by the coordination number of the coordination compound obtainable from the particular salt. If more than one coordination number is known for a given metal ion (e.g., 2 and 4 in the case of cupric ion), little or no excess over stoichiometry of ligand-forming material is used in making the lower coordination number ($n = 2$) species, while considerable excess can be used for the $n = 4$ species. In an alternative method, higher or lower numbers of ligands can be derived from previously prepared and isolated coordination compounds by adding or driving off ligands, e.g. converting the $n = 4$ species to the $n = 2$ species by carefully driving off two moles of the imidazole from a mole of the $n = 4$ species.

Examples of coordination compounds of formula (V) made for use in this invention are:

$CuL_4(SO_3CF_3)_2$
$CuL_2(SO_3CF_3)_2$
$CuL_3(SO_3CF_3)$
$CuL_4(SO_3CF_2CF_3)_2$
$CoL_6(SO_3CF_3)_2$
$CoL_6(SO_3CF_2CF_3)_2$
$NiL_6(SO_3CF_3)_2$
$NiL_6(SO_3CF_2CF_3)_2$
$NiL_6(SO_3CF_2CF_2CF_3)_2$
$CdL_2(SO_3CF_3)_2$
$ZnL_6(SO_3CF_3)_2$ wherein L is as defined previously in formula (V).

Mixtures of such coordination compounds with themselves or with conventional curing agents can be used to provide a wide variety of curing capabilities and to vary the properties of the cured materials. An extensive discussion of mixtures containing conventional curing agents can be found in the aforementioned DOS 1,904,641.

The compounds of formula (V) can best be described as latent "initiators" in that, upon dissociation, they are particularly effective in initiating ring opening reactions or the like which lead to polymerization and/or crosslinking of strained heterocycle-containing compounds. The most useful result of such reactions is gelling or solidification of liquid systems. Liquid, curable epoxy systems can thus be "cured" or hardened to solids having a Barcol hardness of, for example, at least 80. In short, the initiators of this invention are particularly useful as curing agents (also known as "hardeners" or "activators"). The properties of the resulting cured systems are the same as or similar to the properties obtained from a low temperature cure with free imidazole.

The peak exotherm temperature produced when compounds of Formula (V) are used as curing agents — particularly in commercially significant curable epoxy systems such as the monomeric aliphatic epoxides, the curable glycidyl ethers and polyglycidyl ethers, the aliphatic epoxides modified with glycols, the glycidyl ethers of novolak-type resins, and the like — tends to be significantly lower (e.g. more than 50° C. lower) than peak temperatures resulting during the curing of these same epoxy systems with the prior art metal salt-imidazoles, particularly when these epoxy systems are quickly brought to their cure temperatures. Indeed, it is a feature of this invention that suitable curable systems containing the initiators of this invention can be controlably cured using a "hot entry" technique, wherein the curable system is plunged into a preheated bath or atmosphere and thereby brought to the cure temperature almost instantaneously (in substantially less than 5 minutes, for example).

This lowering of the peak exotherm temperatures is less dramatic and may even be negligible during the cure of cycloaliphatic epoxides. However, in contrast to the latent initiators or curing agents of this invention, many of the preferred prior art metal salt-imidazole latent curing agents, e.g. imidazole-copper (II) chloride and imidazole-cobalt (II) chloride, appear to be inoperative as curing agents for cycloaliphatic epoxides.

There is no simple theoretical explanation for these differences between the present invention and the prior art, and this invention is not, in any event, dependent upon any theoretical explanation. The noncoordinated metal salts per se, i.e. the metal fluoroalkylsulfonates, can be used as latent curing agents for epoxides and the like according to the teachings of J. E. Kropp, U.S. patent application Ser. No. 813,758, filed Apr. 4, 1969. However, such metal salts, e.g. Co (II), Cu (II), and Ni (II) trifluoromethane sulfonate produce high peak exotherm temperatures; e.g., for a system containing a gram of one of these metal salts mixed with ten grams of epoxy resin, the peak exotherm is more than 150° C. higher than the "hot entry" bath temperature of 140° – 160° C. It is not understood why the combination of two catalytic species (the imidazole nucleus and the fluoroalkyl sulfonate anion) in a coordination compound produces improved effects such as better control over the exotherm during curing. The literature (including the aforementioned DOS reference) does not suggest this improvement. The DOS does not teach that the choice of anion is critical; still less does it teach the use of salts containing fluorinated alkyl sulfonate anions, although the structurally analogous trifluoroacetate salts are suggested. Surprisingly, in terms of peak exotherm temperatures during curing of epoxy resins, metal-imidazole trifluoroacetates are not analogous to the corresponding metal-imidazole trifluoromethane sulfonates.

Although this invention is not bound by any theory, studies of the thermal decomposition of metal-salt-imidazole initiators of this invention indicate that, at elevated temperatures, the imidazole or substituted imidazole ligand is fully liberated and de-latentized, thus permitting both the imidazole nucleus and the fluoroalkylsulfonate anion to participate, in some manner, in the initiation reaction.

A further feature of this invention is that the increased control over the exotherms produced during the initiation and subsequent reactions (which reactions provide useful gelation and/or curing effects) is obtained without unduly slowing down these reactions, provided suitable elevated temperatures are used. Thus, while the gel time of an epoxy resin/curing agent system of this invention can be as long as 4 or 5 hours at 100° C., it can be as short as 30 seconds at 200° C. (Gelling or curing initiated at less than 90° C. tends to be far too slow for must uses, and gelling or curing may be uncontrollable at temperatures above 250° C.). In the preferred cure temperature range of 120° – 170° C., complete curing is ordinarily obtained in about 1 – 20 minutes (e.g. about 5 – 15 minutes), and generally speaking the cure time is about the same or slightly longer than cure times of prior art latent curing agents. Since "hot entry" curing can be adequately controlled according to the teachings of this invention, the total time involved in the curing of epoxy systems or the like can be substantially shortened by eliminating or speeding up the slow preheating or de-latentizing cycle necessitated by prior art latent curable epoxy systems.

Thus, the latency of the initiators or curing agents of this invention is apparent even at ambient temperatures as high as 90° C. At 90° C. or lower, the initiation reaction or reactions are not observed for several minutes or hours. At temperatures below 50° C., this period of latency can be indefinitely long. Liquid curable epoxy systems of this invention have been stored at normal ambient temperatures for more than one year, and no traces of gelation have been observed.

For maximum curing efficiency, the preferred curable and gelable liquid systems of this invention contain more than 0.2 parts by weight of initiator per 100 parts by weight (0.2 phr) of the heterocyclic compound, e.g. a curable epoxy resin. Less than 0.2 phr can be used if small amounts of additional curing agents such as dicyandiamide are combined with the metal fluoroalkylsulfonate-imidazole initiator. The upper limit of initiator concentration is fixed more by economic than by theoretical considerations. Thus, amounts up to 25 phr by weight of initiator can be used, but are not necessary, since ordinarily amounts of less than 15 phr by weight will provide effective initiation of a ring opening reaction or the like. It is significant that, in any event, the ratio of equivalents of activatible imidazole to equivalents of reactive heterocycle (e.g. of epoxy) can be substantially less than 1:1 and generally less than 0.3:1, indicating that an effect in the nature of catalysis is obtained.

In a ten gram sample cylindrical casting of a one-part curable epoxy system of this invention, the casting being about 20 mm in diameter and 30 mm in length, a "hot entry" cure initiated at 140-160° C. and a curing agent concentration of less than 5 wt. % produces a peak temperature during the cure which is well below 275° C. and generally below 225° C. In curing a similar sample casting comprising the polyglycidyl ether of bisphenol A and epichlorohydrin and 5 wt. percent or even 10 wt. percent of an initiator of this invention, peak temperatures as low as 203° C. have been observed. With sample castings containing cycloaliphatic epoxy as the curable material, the peak temperatures observed during curing are generally lower, e.g. 190°-210° C.

The systems which are most readily and controllably attacked by the latent initiators of this invention are compounds, preferably polymers (including dimers and trimers, copolymers, prepolymers, etc.) containing an average of at least one (preferably at least two) strained heterocyclic rings per average molecular weight and an equivalent weight (per heterocycle) of at least about 100, though lower equivalent weight materials are also operative. Theoretically, saturated rings of less than 5 members are under strain and are substantially inflexible, while saturated rings of greater than 6 members are under strain but are flexible, permitting at least some relief of strain, six-member rings being strain-free in the "chair" or "boat" configuration. Most commercially significant are the three-member rings wherein the hetero-atom contains an unbonded pair of electrons, e.g. a 3-member O-heterocycle (i.e. the 1,2-epoxy or oxirane group) or N-heterocycle.

Compounds containing the 1,2-epoxy group are also known as epoxides and can be mono- or polyepoxides. Curable one-part epoxy systems can be obtained according to this invention by simply mixing together the initiator of this invention (with or without additional curing agents or initiators) and one or more of these mono- or polyepoxides at ambient temperatures. If desired, a conventional organic solvent can be used to facilitate mixing. Admixture of the initiator and a conventional curable epoxy resin imparts a color to the system prior to curing. Upon reaching the cured state, the conventional amber or brown color is observed. The uncured system is insensitive to water, hence the results of initiating the curing reactions do not vary due to atmospheric humidity.

Epoxides suitable for use in this invention can be aliphatic, cycloaliphatic, aromatic or heterocyclic and will typically have an epoxy equivalency (i.e. the number of epoxy groups contained in the average molecule) of from 2.0 to 6.0 preferably 2 or 3, this value being the average molecular weight of the epoxide divided by the epoxide equivalent weight. The epoxy equivalent weight, which is determined by multiplying the sample weight by 16 and dividing by the number of grams of oxirane oxygen in the sample, is typically greater than 100 for commercially useful curable systems. The lower the equivalent weight, the higher the exotherm for a given sample weight. Typical of such epoxides are the glycidyl-type epoxy resins, e.g. the diglycidyl ethers of polyhydric phenols and of novolak resins, such as described in "Handbook of Epoxy Resins", by Lee and Neville, McGraw-Hill Book Co., New York (1967).

Particularly useful epoxides which can be used in this invention are those which contain one or more cycloaliphatic epoxide groups such as the epoxycyclohexanecarboxylates, typified by 3,4-epoxycyclohexylmethyl 3,4-epoxycyclohexanecarboxylate, 3,4-epoxy-2-methylcyclohexylmethyl 3,4-epoxy-2-methylcyclohexanecarboxylate, and bis(3,4-epoxy-6-methylcyclohexylmethyl) adipate. For a more detailed list of cycloaliphatic epoxides of this nature, reference is made to U.S. Pat. No. 3,117,009.

Further epoxides which are useful in the practice of this invention include glycidyl ether monomers of the formula

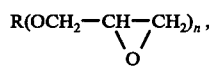

where R is alkyl or aryl and $n$ is an integer of 1 to 6. An example is the glycidyl ethers of polyhydric phenols obtained by reacting a polyhydric phenol with an excess of chlorohydrin, such as epichlorohydrin, e.g. the diglycidyl ether of Bisphenol-A. Further examples of epoxides of this type which can be used in the practice of this invention are described in U.S. Pat. No. 3,018,262.

Still further examples of epoxides are disclosed in DOS 1,904,641, cited previously.

The N-heterocyclic materials suitable for use in this invention include those having the structures

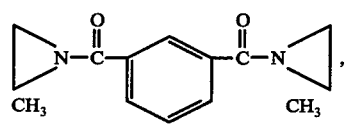

-continued

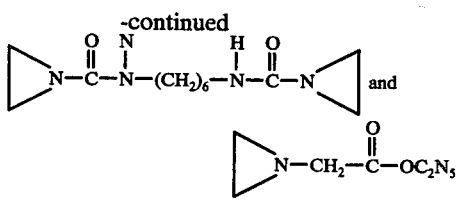

There are a host of commercially available epoxides which can be used in this invention, including the diglycidyl ether of Bisphenol A (e.g., Epon 828 and DER 332), vinylcyclohexene dioxide (e.g., ERL-4206), 3,4-epoxycyclohexylmethyl-3,4-epoxycyclohexane carboxylate (e.g., ERL-4221), 3,4-epoxy-6-methylcyclohexylmethyl-3,4-epoxy-6-methylcyclohexane carboxylate (e.g. ERL-4201), bis(3,4-epoxy-6-methylcyclohexylmethyl)adipate (e.g., ERL-4289), bis(2,3-epoxycyclopentyl)ether (e.g. ERL-0400), aliphatic epoxy modified with polypropylene glycol (e.g., ERL-4050 and ERL-4052), dipentene dioxide (e.g. ERL-4269), epoxidized polybutadiene (e.g., Oxiron 2001), silicone epoxy (e.g., Syl-Kem 90), 1,4-butanediol diglycidyl ether (e.g., Araldite RD-2), polyglycidyl ether of phenolformaldehyde novolak (e.g., DEN-431 and DEN-438) resorcinol diglycidyl ether (e.g., Kopoxite), and epoxidized unsaturated glyceryl esters of carboxylic acids having more than six carbon atoms, e.g. epoxidized soybean oil. Low equivalent weight acetals such as trioxane and low equivalent weight epoxide monomers such as propylene oxide, the epihalohydrins, glycidol, etc., are also operative in this invention, bearing in mind the difficulty of controlling the relatively high exotherm (due to the low equivalent weight).

Any of the conventional filler materials can be added to the curable systems of this invention including pigments and the like. Curable systems of this invention can be used in the conventional manner to make coated, impregnated, or molded products, e.g. structural panels and the like. The low exotherm evolved by systems of this invention is particularly advantageous in the making of molded products with relatively thick or massive shapes, i.e. as opposed to film or layer-like objects.

In the following non-limiting Examples, all parts are by weight unless otherwise indicated.

EXAMPLE 1

Preparation of [Zn(C$_3$N$_2$H$_4$)$_4$](SO$_3$CF$_3$)$_2$

Zinc (II) perfluoromethane sulfonate (20 gm – 0.04 mol) was mixed with solid imidazole (15 gm – 0.22 mol) in a 150 ml. beaker on a hot plate and the mixture was melted. After cooling the product, it was placed in the thimble of a soxhlet extractor and the excess imidazole was extracted by conventional soxhlet extraction using toluene as a solvent.

Calculated: 10.3% Zn
Found: 10.3% Zn

EXAMPLES 2 – 4

Preparation of Co(II), Ni(II), and Cu(II)-Imidazole-Perfluoromethane Sulfonate

The procedure of Example 1 was followed in substance, except that 0.11 mol of Co(II), Ni(II), or Cu(II) perfluoromethane sulfonate was dissolved in 300 ml. methanol and reacted with 0.7 mol (in the case of the cobalt and nickel salts) or 0.5 mol (in the case of the copper salt) of imidazole. The solution was concentrated by evaporation to 150 ml. Addition of 200 ml. of ether precipitates the desired salt. The salt was filtered and washed with ether and dried at room temperature. The following products were obtained: (L = imidazole)

| Ex. | Product (L=C$_3$N$_2$H$_4$) | % Metal Calc. | % Metal Found | m.p. |
|---|---|---|---|---|
| 2 | CoL$_6$(SO$_3$CF$_3$)$_2$ | 10.3 | 10.3 | 210° C. |
| 3 | NiL$_6$(SO$_3$CF$_3$)$_2$ | 7.7 | 7.6 | 270° C. |
| 4 | CuL$_4$(SO$_3$CF$_3$)$_2$ | 10.2 | 10.4 | 170° C. |

The above procedure, when carried out with the appropriate molar amounts of 2-ethyl-4-methyl imidazole provided the corresponding hexa- and tetra-2-ethyl-4-methyl imidazole metal trifluoromethanesulfonates as colored precipitates. These precipitates were purified by washing with ether and drying in vacuo.

The di-imidazole copper(II) perfluoromethane sulfonate was made by reacting precisely 0.25 mol of copper-(II) perfluoromethanesulfonate with slightly more than 0.05 mol of imidazole in methanol. Copper(I) triimidazole perfluoromethanesulfonate was obtained by converting copper(I) chloride (see Brauer, *Handbook of Preparative Inorganic Chemistry*, Vol. II, 2nd Ed., Academic Press, New York, 1965, page 1005) to copper(I) perfluoromethanesulfonate with perfluoromethyl sulfonic acid and reacting with slightly more than three times the molar amount of imidazole.

EXAMPLE 5

Preparation of Copper(II) Tetraimidazole-Perfluoro(lower alkyl) Sulfonates

Approximately 0.5 mole of n-C$_4$F$_9$SO$_3$H was reacted with slightly more than 0.25 mol CuCO$_3$ suspended in water. The mixture was heated and filtered from unreacted CuCO$_3$. The blue filtrate was slowly evaporated on a hot plate. The salt obtained was a waxy solid.

This product (0.11 mol) was dissolved in CH$_3$OH and imidazole (0.5 mol) was added slowly to the solution. Complexing with imidazole was indicated by the deep blue color of the solution. The solution was evaporated and addition of ether caused precipitation of a blue-violet powder. The powder was found to have a melting point of about 190° C.

The same procedure was followed with n-C$_8$F$_{17}$SO$_3$H to obtain the perfluorooctylsulfonate salt and from this the corresponding Cu(II) tetra-imidazole of perfluorooctylsulfonate coordination compound. The melting point of this coordination compound was 210° C.

Both of the coordination compounds of this Example were found to be latent initiators capable of efficiently curing 10 g. samples of "Epon 828" (Shell trade-mark) at temperatures above 100° C. The low exotherms evolved during these cures (for cylindrical castings about 20 mm. in diameter × 0.30 mm. in length plunged into a preheated 150° C. bath) resulted in peak exotherm temperatures of about 197° C; cf. Example 8.

EXAMPLE 6

Gel Time Determination

The varying degrees of latency of a curing agent of this invention were demonstrated by determining the gel time (time required for the system to "set") of a mixture of one gram of the product of Example 2 and 10 grams of "Epon 828" (the polyglycidylether of Bisphenol A and epichlorohydrin), i.e. about 10 phr of curing agent. The resulting viscous curable system, which was pink in color, did not gel at room temperature. At 100° C., the gel time was 68 minutes, indicating that some latency remained even at this temperature, since a similar curable system containing free imidazole had a gel time of about 5 minutes at 100° C. At 120° C., the gel time was still somewhat longer than that for free imidazole: 9 minutes, 15 seconds, as against 2 minutes, 50 seconds. At 140°, 160°, and 180° C., however, the differences in gel time between the curing agent of Example 2 and free imidazole were insignificant: 2 minutes, 30 seconds, and 20 seconds, respectively, as against 1 minute, 24 seconds, and 15 seconds.

EXAMPLE 7

Curing of Cycloaliphatic Epoxy Systems

One gram of each of the products of Examples 1–4 was mixed with 10 g. "Ciba CY-179" (3,4-epoxycyclohexylmethyl 3,4-epoxycyclohexanecarboxylate, i.e. E—CH$_2$—O—CO—E, wherein E is 3,4-epoxycyclohexyl) to provide the curable systems to be tested. Thus, in each case 10 phr of the mixture was the metal perfluoromethyl-sulfonate-imidazole. In each case the mixture was unreactive and remained a viscous liquid at room temperature. Even at 100° C., the metal perfluoromethylsulfonate-imidazoles remained latent for about 55 minutes. However, when the mixtures were heated to 150° C., the following results were observed: (L = imidazole)

TABLE I

| Ex. | Curing Agent (10 wt. %) | Cure Time (min.) at 150° C. | Barcol Hardness | Color of System Prior to Cure |
|---|---|---|---|---|
| 1 | ZnL$_4$(SO$_3$CF$_3$)$_2$ | 10 | 84 | Colorless |
| 2 | CoL$_6$(SO$_3$CF$_3$)$_2$ | 10 | 84 | Pink |
| 3 | NiL$_6$(SO$_3$CF$_3$)$_2$ | 10 | 86 | Blue |
| 4 | CuL$_4$(SO$_3$CF$_3$)$_2$ | 10 | 85 | Violet |

A compound made according to Example 3 of DOS 1,904,641 did not cure the "CY-179", even at 150° C. A compound made from cobalt (II) chloride and imidazole in the imidazole-to-salt molar ratio of 6:1 also failed to cure the system at 150° C.

EXAMPLE 8

Exotherms During "Hot Entry" Cures

In the following "hot entry" cures, an oil bath was preheated to 150° C. and maintained at this temperature (±1° C.) with mechanical stirring. Ten gram samples of resin were poured at room temperature into a 20 × 100 mm thin-walled vessel, filling the vessel about one-third full. An appropriate amount of curing agent, also at room temperature, was rapidly mixed into the resin. The vessel was immediately placed in the oil bath, and a thermocouple was inserted into the middle of the resin/curing agent mixture, permitting accurate temperature measurement with a potentiometer system. In each test of a sample, the sample was brought to 150° C. in approximately 60 seconds. In the following table, the "peak exotherm temperature" data refers to the highest temperature observed during curing. The peak exotherm above the cure temperature can be derived from this data by subtracting 150° C.

The tabulated data of Table II clearly indicate that the initiators or curing agents of this invention cure a wider variety of epoxides and/or cure epoxides with significantly lower exotherms than the curing agents of DOS 1,904,641 or the metal perfluoroalkylsulfonates per se.

TABLE II

| | 150° C. "Hot Entry" Cures (L = imidazole) | | | |
|---|---|---|---|---|
| | "Epon 828" | | "Cy 179" | |
| Compound | phr of curing agent | Peak exotherm temperature (° C.) | phr of curing agent | Peak exotherm temperature (° C.) |
| Co(SO$_3$CF$_3$)$_2$ | 4 | 308 | 4 | high exotherm |
| Cu(SO$_3$CF$_3$)$_2$ | 4 | 308 | 4 | high exotherm |
| Ni(SO$_3$CF$_3$)$_2$ | 4 | 317 | 4 | high exotherm |
| Ni(CO$_2$CF$_3$)$_2$ | 4 | * | * | * |
| Ni(CO$_2$CF$_3$)$_2$ | 10 | * | * | * |
| L$_6$NiCl$_2$ | 4 | 339 | 10 | 242 |
| L$_4$CuCl$_2$** | 4 | 300 | * | * |
| L$_4$CuCl$_2$ | 10 | 341 | 10 | 190 |
| L$_6$CoCl$_2$ | 4 | 324 | * | * |
| L$_6$CoCl$_2$ | 10 | 332 | 10 | 249 |
| L$_6$Ni(CO$_2$CF$_3$)$_2$ | 4 | 325 | 10 | 245 |
| L$_4$Cu(SO$_3$CF$_3$)$_2$ | 10 | 209 | 10 | 190 |
| L$_6$Co(SO$_3$CF$_3$)$_2$ | 10 | 203 | 10 | 207 |
| L$_6$Ni(SO$_3$CF$_3$)$_2$ | 4 | 207 | 10 | 205 |

*No reaction
**Example 3 of DOS 1,904,641

What is claimed is:

1. A compound of the formula $$ML_n(O-SO_2-R_f)_m$$

wherein
M is a metal selected from Groups VIII, IB and IIB of the Periodic Table,
n is a coordination number of M ranging from 2 to 8,
R$_f$ is a perfluorinated alkyl or cycloalkyl group of 1–18 carbon atoms,
m is the valence of M, and
L is an imidazole of the formula

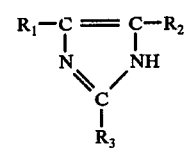

wherein
R$_1$, R$_2$, and R$_3$ are the same or different and are selected from the group consisting of hydrogen, phenyl, methyl, benzyl and ethyl.

2. A compound according to claim 1, wherein R$_f$ is a perfluorinated alkyl or cycloalkyl radical containing 1 – 8 carbon atoms.

3. A compound according to claim 1 wherein n is a whole number from 2 to 8, m is a whole number from 1 to 3, and M is selected from the group consisting of iron, cobalt, nickel, copper, cadmium, zinc, and silver.

4. A compound according to claim 1 selected from the group consisting of CuL$_4$(SO$_3$CF$_3$)$_2$, CuL$_2$(SO$_3$CF$_3$)$_2$, CuL$_3$(SO$_3$CF$_3$), CuL$_4$(SO$_3$CF$_2$CF$_3$)$_2$, CoL$_6$(SO$_3$CF$_3$)$_2$, CoL$_6$(SO$_3$CF$_2$CF$_3$)$_2$, NiL$_6$(SO$_3$CF$_3$)$_2$, NiL$_6$(SO$_3$CF$_2$CF$_3$)$_2$, NiL$_6$(SO$_3$CF$_2$CF$_2$CF$_3$)$_2$, CdL$_2$(SO$_3$CF$_3$)$_2$, and ZnL$_6$(SO$_3$CF$_3$)$_2$ wherein L is as defined in claim 11.

5. A compound according to claim 1 wherein L is imidazole.